United States Patent [19]
Fayram et al.

[11] Patent Number: 5,792,199
[45] Date of Patent: Aug. 11, 1998

[54] PACEMAKER HAVING RATE RESPONSIVE TRANSDUCER AND METHOD FOR OPERATING SAME

[75] Inventors: Timothy A. Fayram, Gilroy; Bruce Kirkpatrick, Santa Clara, both of Calif.

[73] Assignee: Pacesetter, Inc., Sunnyvale, Calif.

[21] Appl. No.: 900,083

[22] Filed: Jul. 24, 1997

[51] Int. Cl.[6] .................................................. A61N 1/365
[52] U.S. Cl. ............................................................ 607/19
[58] Field of Search .............................. 607/17, 19, 20, 607/32; 600/595

[56] References Cited

U.S. PATENT DOCUMENTS

| | | | |
|---|---|---|---|
| 3,142,796 | 7/1964 | Goldberg et al. | 600/595 |
| 3,486,506 | 12/1969 | Auphan | 607/19 |
| 4,210,149 | 7/1980 | Heilman et al. | 128/419 |
| 4,313,442 | 2/1982 | Knudson et al. | 607/17 |
| 4,428,378 | 1/1984 | Anderson et al. | 128/419 |
| 4,940,052 | 7/1990 | Mann et al. | 128/419 |
| 5,113,869 | 5/1992 | Nappholz et al. | 128/696 |
| 5,709,225 | 1/1998 | Budgifvars et al. | 607/17 |

*Primary Examiner*—William E. Kamm
*Attorney, Agent, or Firm*—Steven M. Mitchell

[57] ABSTRACT

An implantable cardiac pacemaker having a housing containing pacing circuitry, a signal generator, and an electromagnetic transducer. The transducer has an electrical input line connected to the signal generator, and an electrical output line connected to the pacing circuitry. Consequently, a forcing motion on the transducer sends an electrical signal to the pacing circuitry, and operation of the signal generator causes the transducer to vibrate. The pacemaker may also include a disablement switch connected to the signal generator, with the signal generator operating in response to activation of the switch to cause the transducer to generate an audible warning tone while the pacemaker is disabled.

18 Claims, 5 Drawing Sheets

PACEMAKER HAVING RATE RESPONSIVE TRANSDUCER AND METHOD FOR OPERATING SAME

FIELD OF THE INVENTION

The invention relates to cardiac pacemakers, and more particularly to motion sensors for detecting patient activity.

BACKGROUND AND SUMMARY OF THE INVENTION

Implanted cardiac pacemakers have been used to establish a healthy, nominal heart rate in patients whose natural pacing is failed or unreliable. Because a patient's heart rate should vary based on his activity level, pacemakers have employed activity sensors. These are typically piezoelectric transducers mounted within an implanted pacemaker that respond to patient movement by sensing accelerations and generating an electrical signal that is processed to determine a suitable heart rate. If little or no acceleration is detected, the rate will be set to an established baseline appropriate for a resting condition. If accelerations of a frequency and amplitude corresponding to vigorous activity are detected, the pacing rate is increased to a higher rate; intermediate accelerations lead to intermediate pacing rates.

Piezoelectric transducers can output a wide frequency range that extends to high frequencies of motion that are well beyond the low 0.5–10 Hz frequencies associated with patient activity requiring increased pacing rates. Therefore, conventional pacemakers must use filtering circuitry to avoid burdening the signal processing circuitry with high frequency signals that are not of interest, and which may lead to unwanted results. Such filtering circuitry may add to the cost and complexity of pacemakers. Also, the low power signals output by piezoelectric transducers require preamplification circuitry before processing, further increasing cost and complexity.

Piezoelectric transducers require power for sensing operation, reducing the useful life of a battery-powered implanted pacemaker. Further, piezoelectrics may suffer from a voltage offset problem in which they do not return to a zero voltage when at rest, but continually output a low voltage that decays more slowly than would be desirable for activity sensing purposes. This is especially a concern in the low frequencies of interest in the 2–3 Hz range.

Existing implanted pacemakers have an external switching feature that permits temporary disablement without surgical access to the device. Typically, the pacemaker is provided with an internal reed switch having a ferromagnetic reed element, and the switch is opened by placement of a magnet on the patient's skin immediately above the device, the magnetic field penetrates the patient's tissue to lift the reed and open a circuit. When the magnet is withdrawn, the reed returns to a closed position, and pacemaker functions are reenabled. Preferably, such devices also have audible alarms that generate a tone to remind the patient and doctor while the device is disabled, and to provide assurance that the device is enabled when the tone stops. Although advantageous, such tone generators are an additional component, adding to the cost and complexity of a pacemaker.

The present invention overcomes the limitations of the prior art by providing an implantable cardiac pacemaker having a housing containing pacing circuitry, a signal generator, and an electromagnetic transducer. The transducer has an electrical input line connected to the signal generator, and an electrical output line connected to the pacing circuitry. Consequently, a forcing motion on the transducer sends an electrical signal to the pacing circuitry, and operation of the signal generator causes the transducer to vibrate. The pacemaker may also include a disablement switch connected to the signal generator, with the signal generator operating in response to activation of the switch to cause the transducer to generate an audible warning tone while the pacemaker is disabled.

DETAILED DESCRIPTION OF A PREFERRED EMBODIMENT

Figure 1:
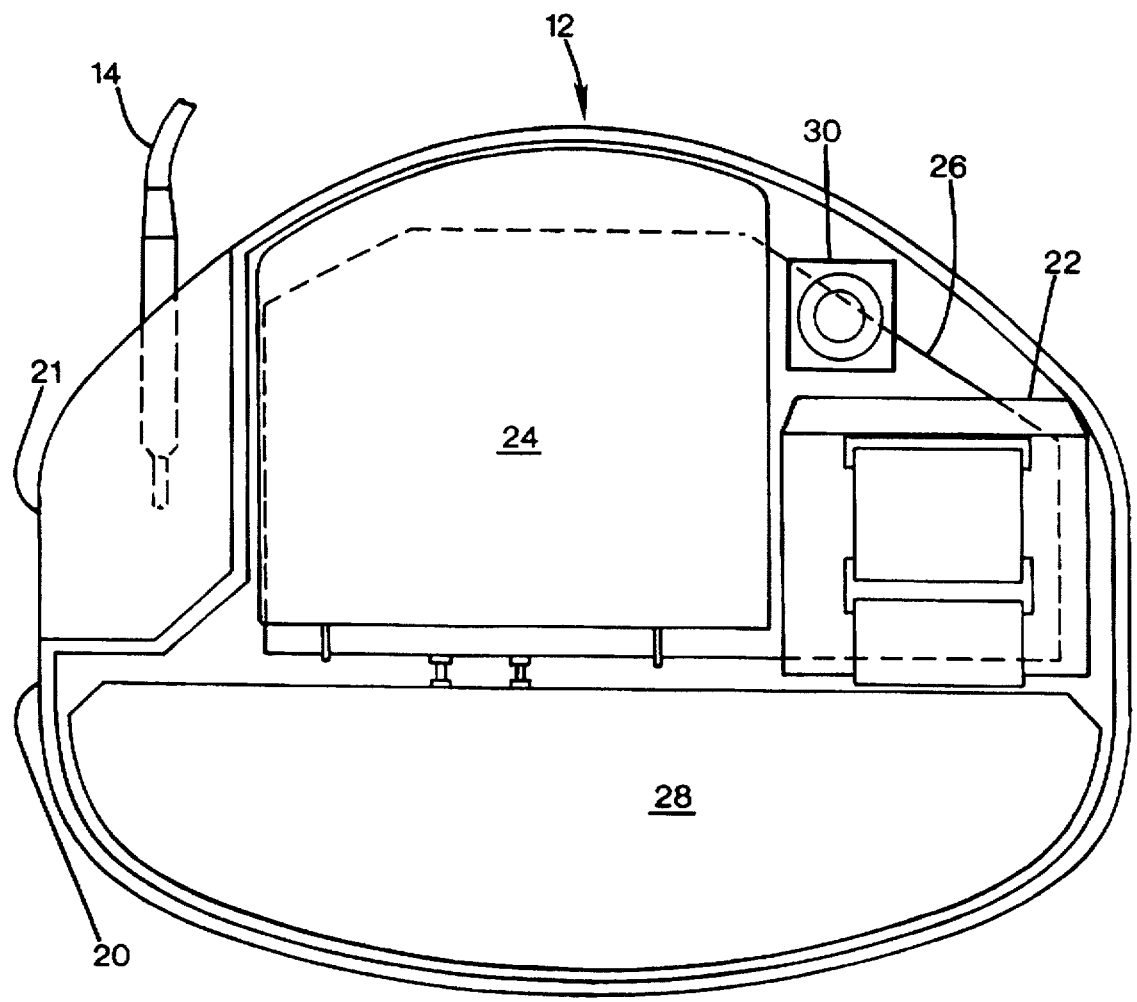
FIG. 1 shows an implantable defibrillator/pacemaker having a transducer according to a preferred embodiment of the present invention.

FIG. 1 illustrates a defibrillator/pacemaker 12 for pectoral implantation. An endocardial lead set 14 extends from the unit, through a vein, and into the patient's heart. The defibrillator/pacemaker 12 includes an outer housing 20 that includes a connector portion or header 21 for attachment of the lead set 14. The housing 20 contains a transformer 22, a battery 24, printed circuit assembly 26 containing pacing and defibrillation circuitry, and two capacitors 28. The printed circuit assembly 26 connects 4 to the lead set 14 so that it may sense and analyze electrical signals from the heart, and control the delivery of an appropriate therapy such as a high voltage shock, or a pacing pulse at a rate based on an activity signal generated by an electromagnetic transducer 30.

Figure 2:
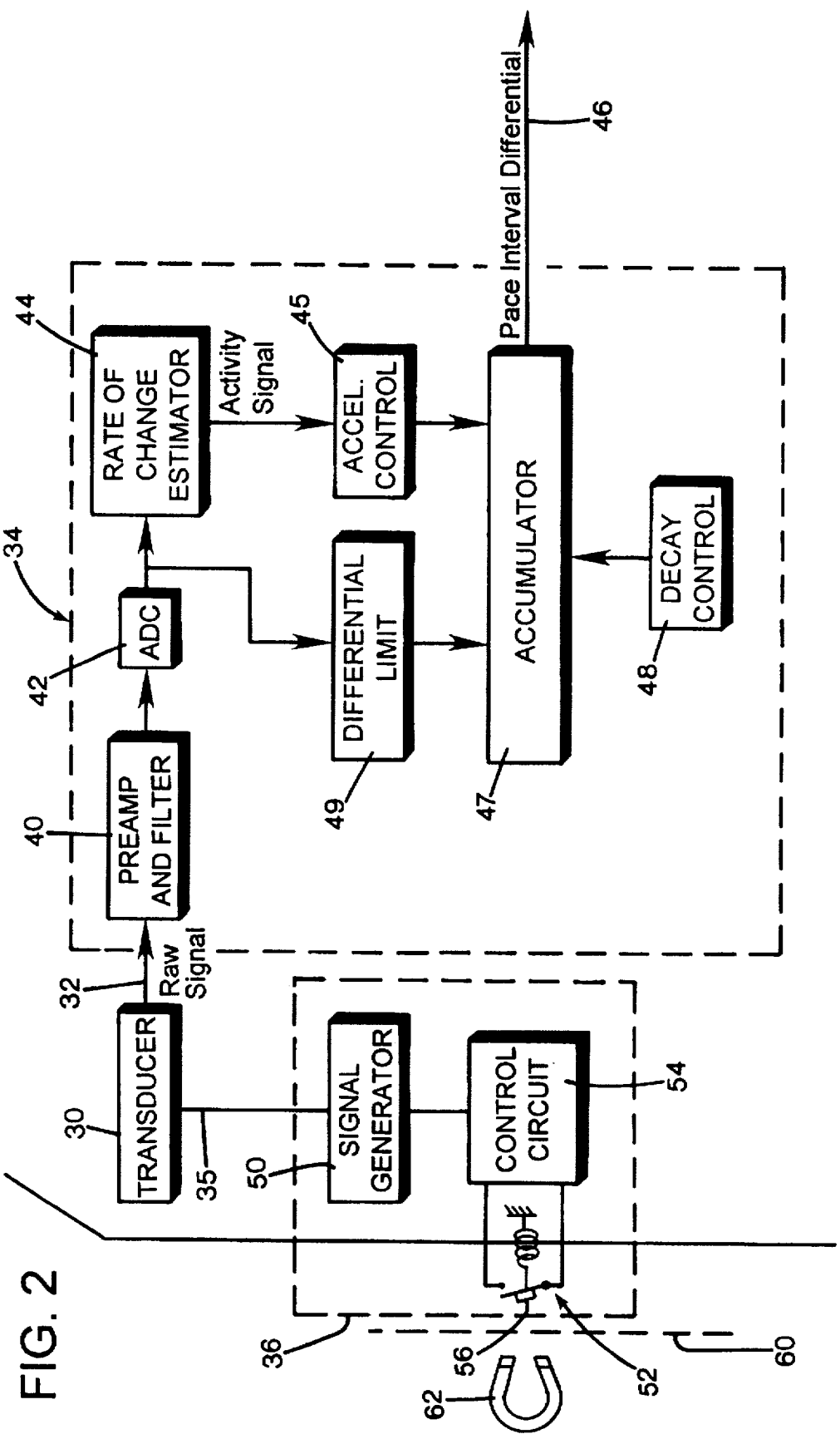
FIG. 2 is an electronic block diagram of selected portions of the circuitry of the embodiment of FIG. 1.

FIG. 2 shows an electronic block diagram showing the components and systems connected to the transducer 30. The transducer has an output line 32 connected to pacing circuitry 34, and an input line 35 connected to disablement circuitry 36. The pacing circuitry is conventional, except that it includes a preamp and filter block 40 that is simpler and less critical than in a system using a piezoelectric transducer. The preamp and filter process the initial signal to isolate responses caused by forcing frequencies in the 1–10 Hz range. Alternative embodiments of the invention may dispense entirely with either the preamp or the filter or both. The conventional low pass filter may not be needed due to the inherent properties of the transducer; the significant moving mass is insensitive to high frequency movements. The preamp need not have a high gain because of the high output of the transducer as compared to piezoelectrics; a small or negative gain are all that may be required to provide a calibrated preamp output.

The preamp 40 has an output connected to an analog-to-digital-converter (ADC) 42 that sends a digital acceleration signal corresponding to the acceleration of the transducer, biased to saturate under strenuous exercise. Noise rejection is automatically achieved by the combination of a low resolution ADC with an appropriate bias. The digital acceleration signal is converted to an activity signal by a rate of change estimator 44, which samples the signal at a selected frequency to estimate the transducer's positional rate of change per unit time. An acceleration control element 45 is connected to the output of the rate of change estimator 44 to process the activity signal to provide a quick acceleration in pacing rate at the onset of exercise, and has an output connected to an accumulator 47. A decay control element 48 also feeds the accumulator, and provides a signal that controls the rate by which the pacing rate returns to normal at the termination of exercise.

To provide acceleration of the pacing rate, the accumulator receives the controlled activity signal and generates a monotonically increasing sum up to a limit. The limit is updated in real time based on the peak positional displacement of the transducer so that higher pacing rates may be achieved for more strenuous activity. The decay control 48 periodically subtracts a selected value from the accumulated sum, so that it gradually returns to zero after exercise stops. A differential limit element 49 is connected to the output of the analog-to-digital-converter 42, and has an output connected to an accumulator 47. The differential limit element contains a stored upper limit value that represents the desired maximum pacing rate at the limiting condition when the signal from the transducer is fully saturated.

The disablement circuitry 36 includes a signal generator 50 having an output connected to the input line 35 of the transducer 30. The signal generator generates a 3 volt output signal in the audible frequency range, but below about 2000 Hz to avoid the damping effects of the tissue in which the device is implanted. In the preferred embodiment, a signal at 440 Hz is generated. Preferably, the signal is a square wave at 100–1000 Hz, and the voltage may range between 1–5 volts, with an operating current of 5–10 mA being typical. The use of a low voltage signal is consistent with operating voltages in other pacemaker circuitry components, avoiding the need for a voltage converter, as might be required by a piezoelectric oscillator operating at 12 V.

A magnetically activated disablement switch 52 is connected via a control circuit 54 to the signal generator to activate the generator when the switch is opened. The control circuit is further connected to pacing circuitry and defibrillation circuitry to disable their operation, such as might be desired when a patient is being examined or tested by a physician seeking to determine the patient's cardiac function in the absence of the device.

The switch 52 is a spring-biased normally-closed reed switch having a ferromagnetic element 56 on the switch arm, or an entirely ferromagnetic arm. The switch arm moves through a path substantially perpendicular to the plane of the patients skin surface 60, directly beneath which the device is implanted. Thus, when a magnet 62 is positioned immediately over the device by a physician, the device is disabled, and the transducer emits a tone during the entire period of disablement. When the magnet is withdrawn, the switch closes, and the tone ceases to indicate that the device is now functioning normally in an enabled condition.

Figure 3:
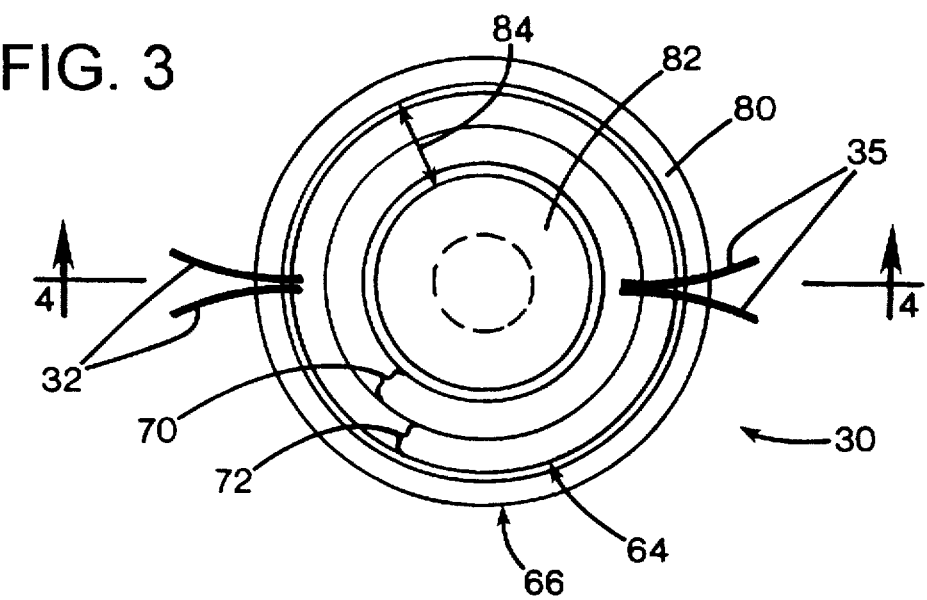
FIG. 3 is a plan view of the transducer of the embodiment of FIG. 1.
Figure 4:
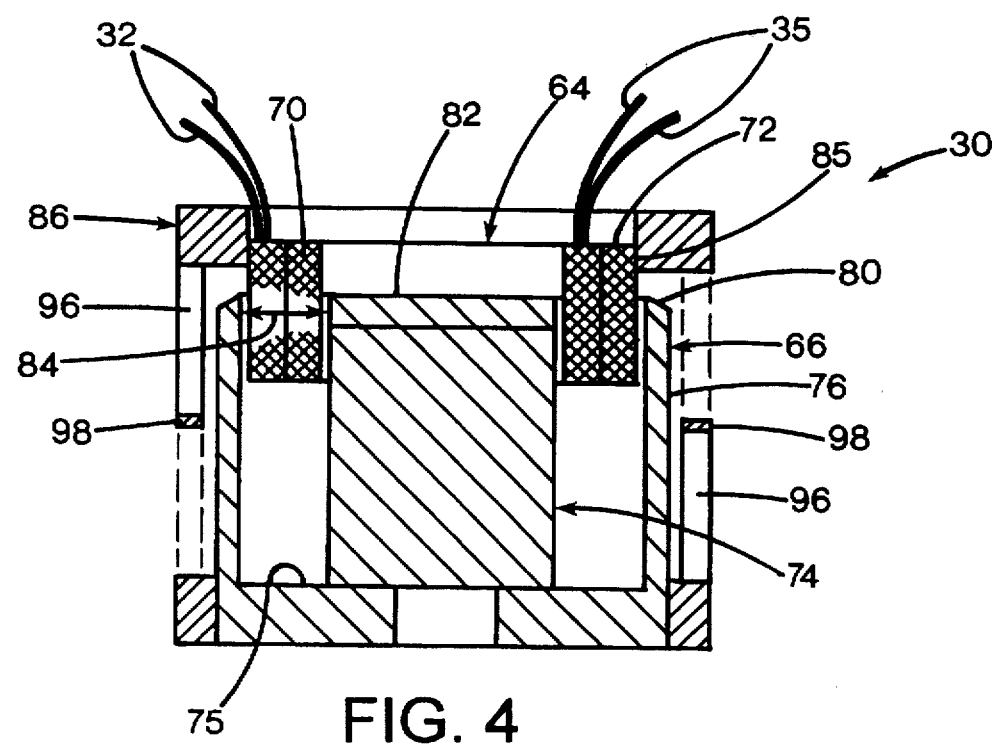
FIG. 4 is a cross sectional side view of the transducer of the embodiment of FIG. 1 taken along line 4—4.

As shown in FIGS. 3 and 4, the transducer 30 includes a coil assembly 64 suspended in a magnetic field generated by a magnet assembly 66. The coil has two electrically independent annular portions, an inner driver portion 70 and an outer sensor portion 72 surrounding the inner portion. In the preferred embodiment, both are formed of 43 gauge copper wire, with the drive portion having 387 turns and 9 layers, and the sensor portion having 344 turns and 8 layers. A first pair of drive wires provides the input line 35 that extends from the ends of the driver portion to the signal generator 50.

A second pair of sensor wires provides the output line 32 that extends from the ends of the sensor portion to the pacing circuitry 34.

The magnet assembly 66 has a cylindrical Neodymium Boron Iron magnet 74 of Neo 35 material, available from Tridus International, Inc. of Paramount, Calif. The magnet has a lower surface secured to the floor 75 of a basin defined in a cylindrical ferromagnetic cup 76. The cup 76 has straight cylindrical sides that extend upward from the floor to an upper edge 80. A circular ferromagnetic pole piece 82 is attached to the upper surface of the magnet, and is coextensive with the upper surface. As the magnet is polarized with one pole at its upper surface and the opposite pole at its lower surface, the cup transmits magnetic flux to the upper edge, where a strong radial magnetic field is formed across the annular magnet gap 84 between the pole piece and the cup edge. The magnetic field flux density in the air gap ranges between 0.6–0.8 Tesla, or 6000–8000 Gauss.

The coil is positioned within the magnet gap, concentric with the pole piece and cup rim, with a limited clearance between the coil surfaces and the magnet assembly of about 0.010 inch (0.25 mm). With the intermediate portion of the coil centered in the gap, a front portion 85 of the coil extends beyond the magnet assembly. A suspension element 86 is connected to the front portion 85 of the coil and to the exterior of the magnet cup at the rear edge surrounding the floor 75. The suspension permits axial motion of the coil relative to the magnet while constraining against lateral and angular motion. Preferably, the suspension with the coil mounted has a natural frequency at a low level, preferably between 0.5 and 10 Hz, but which may range up to about 50 Hz without objectionable damping of the 0–10 Hz motions that generally correlate with patient activity requiring accelerated pacing. In an alternative embodiment, a smaller scale suspension element may be positioned within the magnet cup 76, connected to the floor 75 and to the rear of the coil, surrounding the magnet 74.

Figure 5:
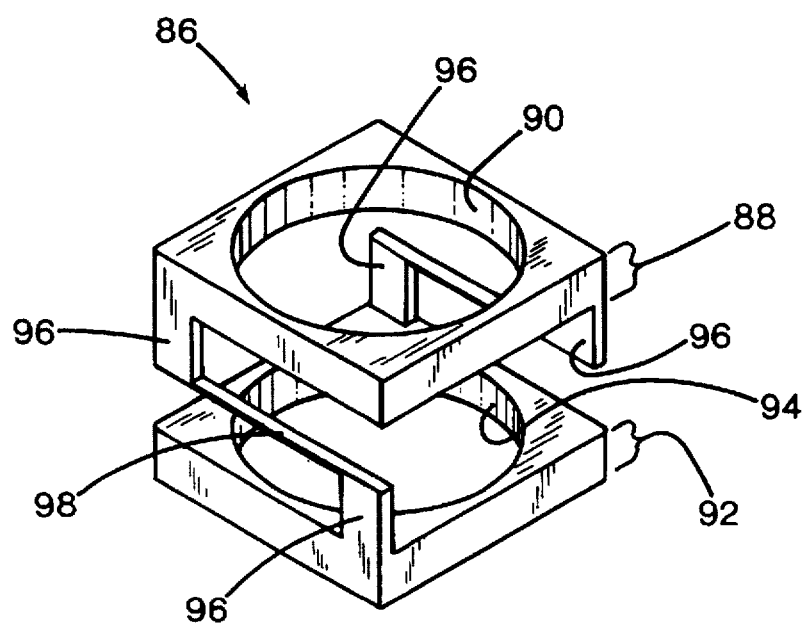
FIG. 5 is an isometric view of a suspension element according to the embodiment of FIG. 1.

As shown in FIG. 5, the suspension element 86 has an upper frame 88 defining an upper bore 90 sized to receive the coil. The suspension is an integral element formed of resilient spring metal such as a steel or copper alloy commonly used for springs. A lower frame 92 defines a lower bore 94 sized to closely receive the magnet assembly. Each frame has a square shape with a pair of rigid posts 96 at diagonally opposed corners protruding toward the opposite frame. The respective diagonals on which the posts of each frame are positioned are perpendicular to each other. Thus, each post on one frame is registered with a corner of the other frame on which there is no post. To provide constrained flexibility, a pair of thin bands 98 extend on opposed sides of the suspension device, each between a first post on the upper frame to a second post on the lower frame. Axial motion of the coil while in sensing mode will impart a gentle cyma recta or S-shape to the bands.

Because of the rotationally symmetrical arrangement of the bands, no stretching or compression of the bands will be required to accommodate axial motion; slight rotation of the upper frame and coil will allow the suspension to move with minimal resistance. This provides the low fundamental frequency of the coil system, which thereby permits substantial axial excursions of +/−0.10 inch (0.25 mm). These displacements allow the generation of an analog signal having a voltage ranging up to about 100 mV without amplification. Because the coil is a passive device that generates its own signal, no power is consumed by the transducer during sensing operation, extending battery life.

Beyond its displacement limits, the suspension has a nonlinear spring constant that resists further displacement and which generates a substantial restoring force. When subjected to substantial acceleration along any axes perpendicular to the coil axis, the suspension is very rigid, and contact between the coil and magnet is avoided. With a typical implantation in a patient's torso, the axis of the coil is aligned parallel to a line perpendicular to the front of the patient's chest. This is believed to effectively detect motions resulting from patient activity, but to ignore motions resulting from environmental jostling, such as those experienced by a motor vehicle passenger.

In the preferred embodiment, the magnet assembly has a diameter of 0.25 inch (6.4 mm), although a range of sizes may be employed for different applications. The mass of the coil may be increased by the addition of static mass or increasing of the wire diameter and axial length to lower the natural frequency of the coil, thereby reducing its sensitivity to higher forcing frequencies that are not pertinent to an estimation of patient activity. The shared use of the transducer saves size and weight compared to using two separate components, but requires that the coil assembly have two electrically independent coils. In an alternative embodiment, a single coil may be used, with electronic switching between the sensing circuitry to the signal generator when the disablement switch is activated.

Figure 6:
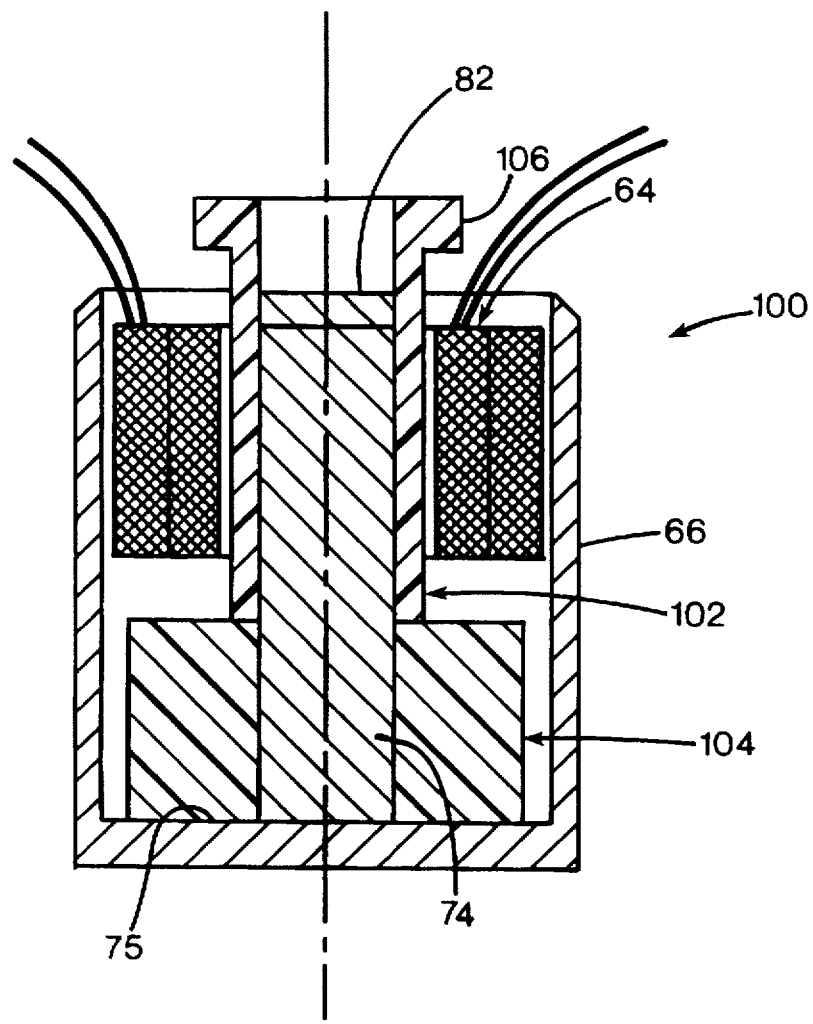
FIG. 6 is a cross sectional side view of the transducer of an alternative embodiment of the invention.

FIG. 6 shows an alternative magnet assembly 100 having a coil assembly 64, metal cup 66, magnet 74, and pole piece 82 all the same or similar to that shown in the preferred embodiment. Instead of the suspension spring, the coil rides on a shouldered sleeve bearing 102 that sheathes the magnet and pole piece. A bored cylindrical bushing 104 closely receives the base of the magnet and is secured against the floor 75 of the cup. The bushing has an outside diameter about as large as the outside diameter of the coil assembly 64, so that it provides a stop to limit travel of the coil toward the floor of the cup.

The sleeve 102 is a bored cylinder having one end butted against the bushing, and a free end protruding from the cup and having a flange 106 extending radially from the free end. The flange has a diameter greater than the inside diameter of the coil, so that the coil is constrained against axial motion beyond the flange. The sleeve is sized to closely receive the magnet, and has an outside diameter sized to receive the coil with a slight clearance gap. Thus, the coil may freely oscillate along the sleeve, limited axially only by the flange and bushing. The gap between the coil and sleeve is narrow enough to prevent the coil from contacting the walls of the cup.

To avoid unwanted wear and potential damage to the coil or the sleeve, the sleeve is formed of a nonconductive low friction polymer such as Delrin AF, available from Dupont of Wilmington, Del. The bushing may be formed of a similar material. In either embodiment, the transducer is oriented in the defibrillator with the coil axis perpendicular to the major plane of the defibrillator, which is generally parallel to the plane of the front of the patient's chest. Thus, motion of a standing or walking patient in a forward or rearward direction will be registered by the transducer, while vertical or lateral motions experienced by vehicle passengers will not. In the alternative embodiment of FIG. 6, the coil rests on the sleeve while the patient is upright. Thus, the frictional force caused by gravity will prevent the coil from moving in response to high frequency and or low amplitude motion signals, further reducing the need for filtering. This is particularly useful when the patient is experiencing vertical or lateral accelerations associated with unimportant frontal-rearward jostling; the increased force of the coil against the sleeve will increase the axial acceleration required to register a signal.

While the invention is described in terms of a preferred and alternative embodiments, the following claims are not intended to be so limited.

We claim:

1. An implantable cardiac pacemaker comprising:

a housing;

pacing circuitry within the housing including pacing rate circuitry controlling a pacing rate of the pacing circuitry as a function of a patient's activity level;

a motion sensor within the housing;

the motion sensor including a magnet assembly defining a magnet gap and a conductive coil movable relative to the magnet assembly in response to motion of the pacemaker and positioned at least in part within the gap; and an electrical connection between the coil and the pacing circuitry such that movement of the coil relative to the magnet assembly induces a current in the coil indicative of motion of the pacemaker and the patient's activity level and sends an electrical signal to the pacing rate circuitry.

2. The pacemaker of claim 1 including a suspension element connected to the magnet assembly and to the coil, the suspension element being flexible to permit constrained relative motion between the coil and the magnet.

3. The pacemaker of claim 2 wherein the suspension element has a natural frequency of less than 100 Hz.

4. The pacemaker of claim 1 wherein the magnet assembly includes an elongated spindle having a spindle axis, and wherein the coil is loosely received on the spindle such that it reciprocates along the spindle in response to a force, and contacts the spindle under acceleration in a direction angularly offset from the spindle axis.

5. The pacemaker of claim 1 including a signal source and a disablement switch coupled to the pacing circuitry within the housing, the disablement switch being operable to disable the pacing circuitry in response to actuation, and wherein the coil is connected to the signal source responsive to actuation of the disablement switch and the signal source delivers a driving signal to the coil causing the coil to vibrate and generate an audible tone.

6. The pacemaker of claim 5 wherein the signal source generates a signal having a frequency of less than 2000 Hz.

7. The pacemaker of claim 5 wherein the disablement switch includes a ferromagnetic portion actuatable by an external magnetic field to disable the pacing circuitry.

8. An implantable cardiac pacemaker comprising:

a housing;

pacing circuitry within the housing including pacing rate circuitry controlling a pacing rate of the pacing circuitry as a function of a patient's activity level;

a signal generator within the housing;

an electromagnetic transducer within the housing which produces an electrical signal in response to motion of the pacemaker; and the transducer having an electrical input line connected to the signal generator, and having an electrical output line connected to the pacing circuitry, such that a forcing motion on the transducer sends an electrical signal to the pacing circuitry indicative of motion of the pacemaker and the patient's activity level, and operation of the signal generator causes the transducer to vibrate.

9. The pacemaker of claim 8 wherein the transducer comprises a coil suspended in a magnetic field.

10. The pacemaker of claim 9 wherein the coil has a sensing portion connected to the output line and a driver portion connected to the input line.

11. The pacemaker of claim 8 wherein the transducer includes a magnet assembly defining a magnet gap and a magnetic field and a single coil element suspended in the magnetic field.

12. A method of operating an implantable cardiac pacemaker having a signal generator, pacing circuitry, a motion transducer, and a disablement switch, the method comprising the steps:

placing the disablement switch in an enabled position; and generating an activity signal in the motion transducer based on accelerative forces on the transducer; and sending the activity signal to the pacing circuitry; and calculating a pacing rate based on the activity signal; and generating a pacing signal as a function of the calculated pacing rate; and subsequently placing the disablement switch in a disabled position; and generating an electrical alarm signal in the signal generator; and sending the alarm signal to the motion transducer; and moving the motion transducer in response to the alarm signal to generate an audible tone.

13. The method of claim 12 wherein the transducer includes a magnet assembly providing a magnetic field and wherein the step of generating an activity signal includes moving a coil element within the magnetic field.

14. The method of claim 13 wherein moving the motion transducer includes moving the coil element within the magnetic field.

15. The method of claim 12 including actuating the disablement switch by positioning a magnet adjacent the pacemaker.

16. The method of claim 12 wherein generating the alarm signal comprises generating a signal with a frequency less than 2000 Hz.

17. An implantable cardiac pacemaker comprising:

a housing;

pacing circuitry within the housing including pacing rate circuitry controlling a pacing rate of the pacing circuitry as a function of a patient's activity level;

a motion sensor within the housing;

a signal source within the housing;

the motion sensor including a magnet assembly defining a magnet gap and a conductive sensor coil movable relative to the magnet assembly in response to motion of the pacemaker and positioned at least in part within the gap;

a conductive driver coil positioned in and movable relative to the magnet assembly and coupled to the signal source whereby the driver coil will vibrate and generate an audible tone in response a driving signal from the signal source; and an electrical connection between the sensor coil and the pacing circuitry such that movement of the sensor coil relative to the magnet assembly induces a current in the coil indicative of motion of the pacemaker and the patient's activity level and sends an electrical signal to the pacing rate circuitry.

18. The pacemaker of claim 17 wherein each of the sensor coil and driver coil is an annulus, and one of the sensor coil and driver coil is concentrically nested within the other.

* * * * *